United States Patent [19]

Mactaggart

[11] Patent Number: 4,602,160
[45] Date of Patent: Jul. 22, 1986

[54] INFRARED CONSTITUENT ANALYZER AND CONTROL SYSTEM

[75] Inventor: John W. Mactaggart, Bolton, Canada

[73] Assignee: Sentrol Systems Ltd., Downsview, Canada

[21] Appl. No.: 536,677

[22] Filed: Sep. 28, 1983

[51] Int. Cl.$^4$ ............................................. G01J 1/00
[52] U.S. Cl. ..................................... 250/341; 356/73
[58] Field of Search ............... 250/341, 339; 356/408, 356/402, 73

[56] References Cited

U.S. PATENT DOCUMENTS

| | | | |
|---|---|---|---|
| 3,601,589 | 8/1971 | McCarty | 356/402 |
| 3,796,887 | 3/1974 | Vincent et al. | 250/565 |
| 3,974,377 | 8/1976 | Steffen | 250/222.1 |
| 4,019,819 | 4/1977 | Lodzinski | 356/73 |
| 4,029,419 | 6/1977 | Schumann et al. | 356/173 |
| 4,120,582 | 10/1978 | DeVries et al. | 356/73 |
| 4,171,918 | 10/1979 | Mactaggart | 356/408 |
| 4,306,835 | 12/1981 | Hurley | 356/43 |
| 4,435,093 | 3/1984 | Krause et al. | 250/346 |
| 4,439,038 | 3/1984 | Mactaggart | 356/408 |

Primary Examiner—Bruce C. Anderson
Assistant Examiner—Richard Hanig
Attorney, Agent, or Firm—Shenier & O'Connor

[57] ABSTRACT

Monochromatic infrared radiation of variable wavelengths between 1.0 and 3.5 microns is directed upon a portion of a moving web, and the spectra of infrared radiation reflected from the web portion and of radiation transmitted through the web portion are separately measured by sensors located on both sides of the web. These spectra are combined to provide an absorption spectrum insensitive to any elastic scattering that is also present. Measures of the contents of the web constituents are generated by least-square fitting the individual absorption spectra of the constituents to the measured absorption spectrum of the web. Means for calibrating the reflectance and transmittance measurements and for keeping the sensor viewing windows free of dirt and dust are also disclosed.

15 Claims, 8 Drawing Figures

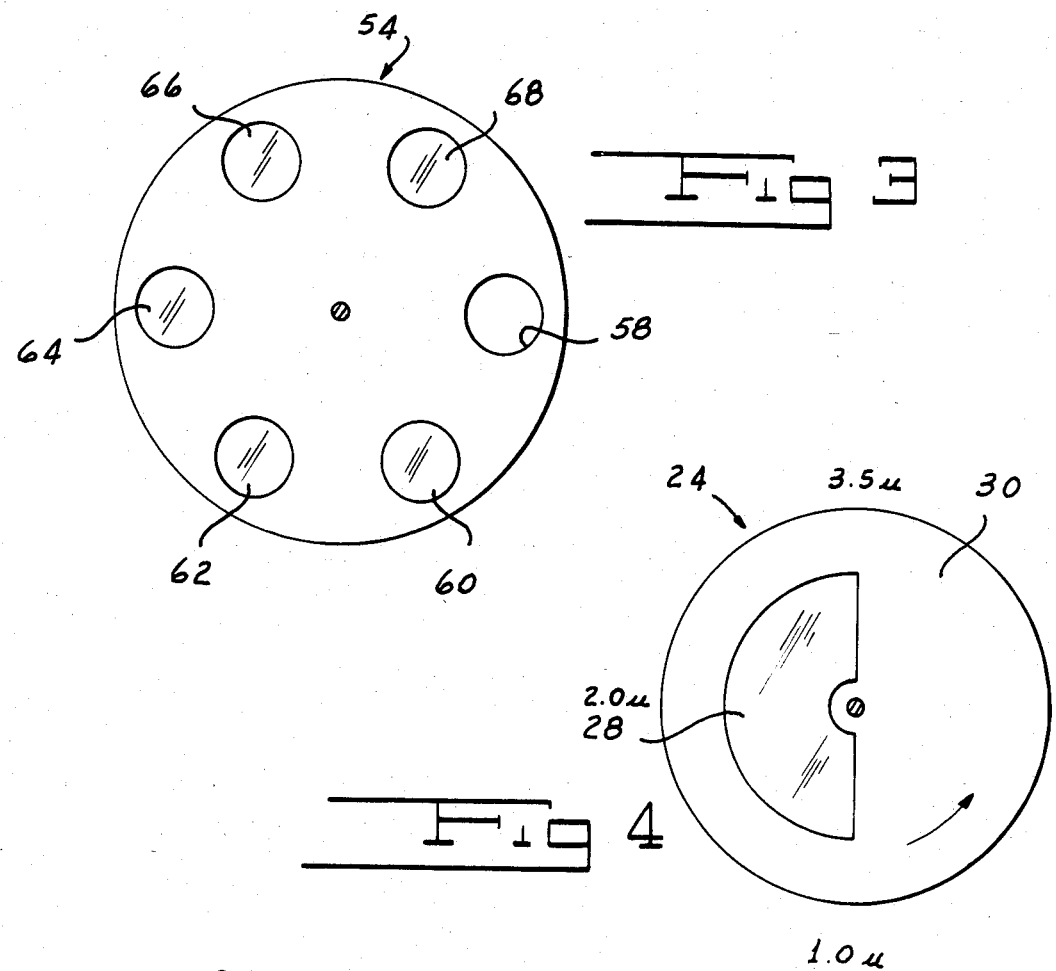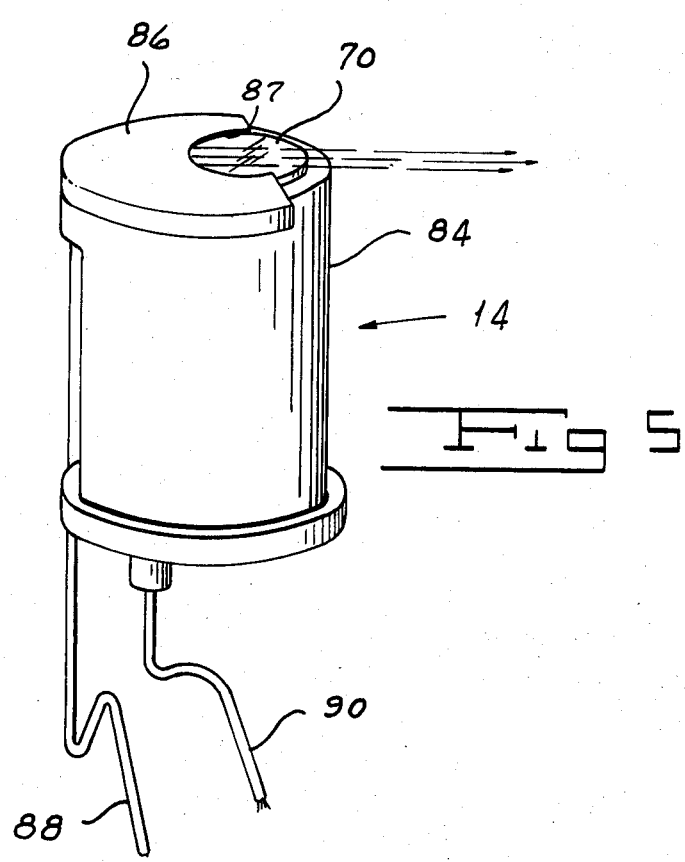

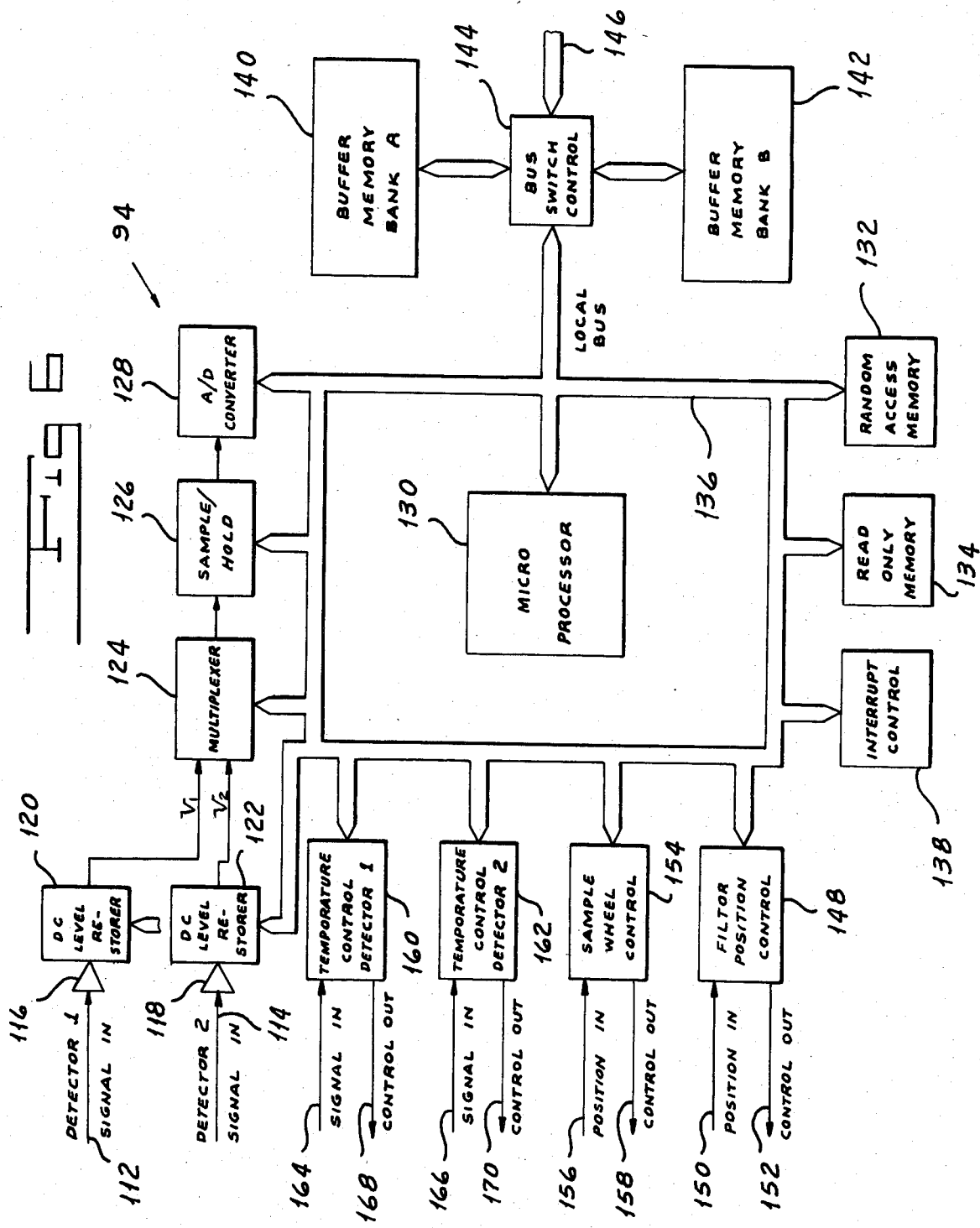

INFRARED CONSTITUENT ANALYZER AND CONTROL SYSTEM

FIELD OF THE INVENTION

My invention relates to a constituent analyzer and, in particular, a method and apparatus for measuring and controlling one or more constituents of a material such as a moving web by infrared techniques.

BACKGROUND OF THE INVENTION

In the manufacture of high-quality papers the use of various binding agents such as latex, urea-formaldehyde and glycerine is becoming more widespread. As a result, the accurate control of the application of these compounds, based upon direct measurements, is economically desirable. In addition, the present web basis-weight and moisture sensors are often adversely affected by the presence of these binders. Therefore, to improve the accuracy of moisture and basis-weight measurements, it is necessary to compensate for the additives contained in the web.

SUMMARY OF THE INVENTION

One object of my invention is to provide a constituent analyzer which produces a direct measurement of the constituents of a material such as a moving web.

Another object of my invention is to provide a constituent analyzer which can measure constituents exhibiting either resonant absorption or preferential scattering over a range of infrared frequencies.

Still another object of my invention is to provide a constituent analyzer which compensates for the effects of elastic scattering.

A further object of my invention is to provide a constituent analyzer which permits regular automatic calibration for the various constituents being measured.

A still further object of my invention is to provide a constituent analyzer which prevents dirt and dust from interfering with the measurement operation.

Other and further objects will be apparent from the following description.

In one aspect, my invention contemplates a method and apparatus for measuring a constituent of a material such as a moving web in which infrared radiation is directed upon the material and separate measurements are obtained of radiation reflected from the material and of radiation transmitted through the material. The constituent content is determined from both measurements, preferably by combining the reflectance and transmittance measurements to obtain a measurement dependent only on the absorption properties of the material.

In another aspect, my invention contemplates a method and apparatus for measuring one or more constituents of a material such as a web in which infrared radiation is directed onto a portion of the material, and a spectrum is obtained of radiation emanating from the portion irradiated. From the measured radiation spectrum, estimated contents of the web constituents are generated which produce a minimum deviation between the predicted radiation spectrum of the material with the estimated contents of the constituents and the measured radiation spectrum.

In yet another aspect, my invention contemplates apparatus in which a jet of gas is directed across the outer surface of the transparent viewing window of the housing of a radiation transducer to prevent the accumulation of contaminants thereon.

BRIEF DESCRIPTION OF THE DRAWINGS

In the accompanying drawings, which form part of the instant specification and which are to be read in conjunction therewith, and in which like reference numerals are used to indicate like parts in the various views:

FIG. 3 is a view of the standard wheel of the apparatus of FIG. 1, along line 3—3 thereof.

FIG. 4 is a view of the filter wheel of the apparatus shown in FIG. 1, along line 4—4 thereof.

FIG. 5 is a perspective view of the housing of the lower sensor head shown in FIG. 1.

FIG. 6 is a schematic diagram of the sensor interface module of the system shown in FIG. 2.

DESCRIPTION OF THE PREFERRED EMBODIMENT

Figure 1:
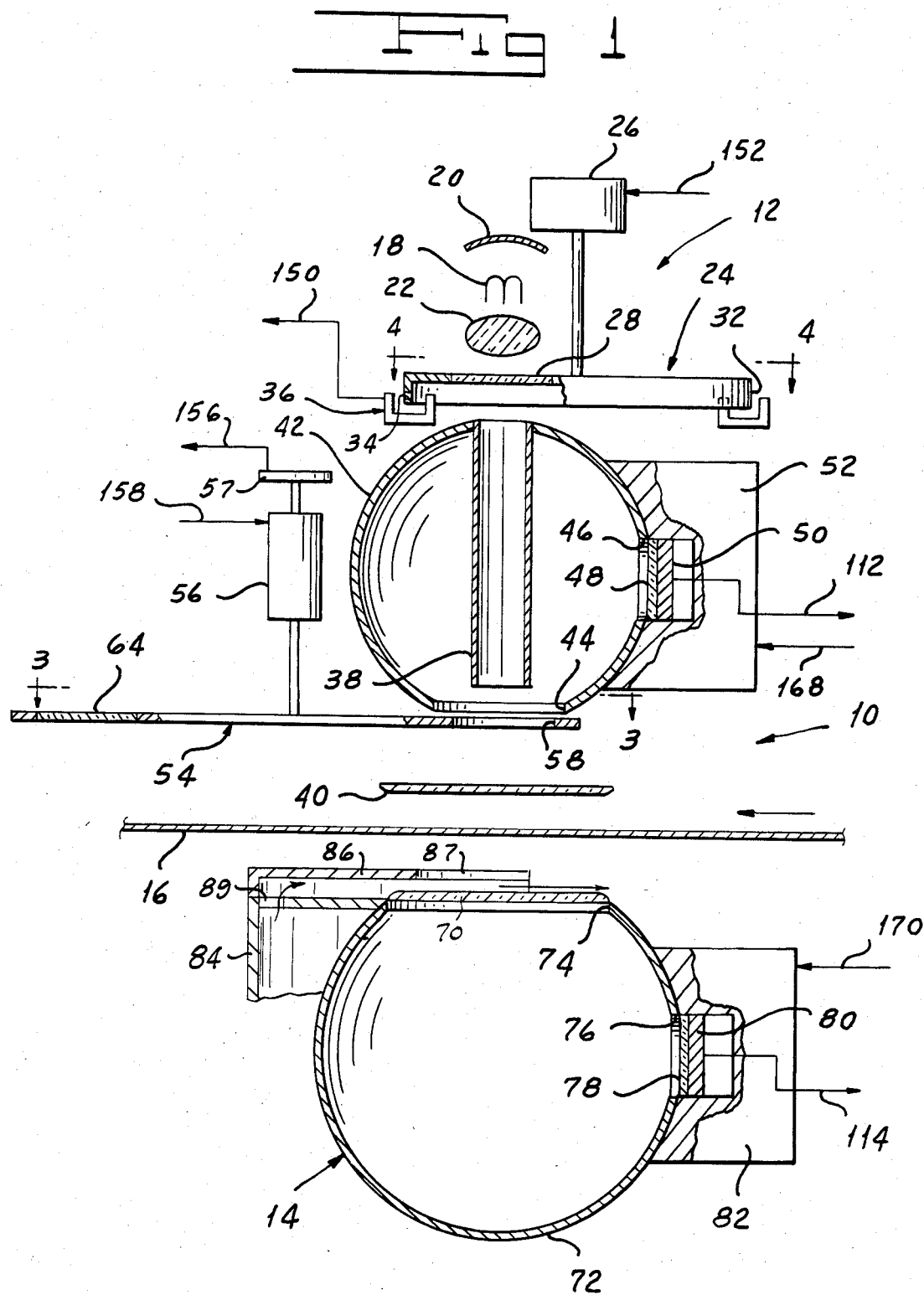
FIG. 1 is a partly schematic fragmentary side elevation of the upper and lower sensor heads of my infrared constituent analyzer and control system, with parts shown in section and with other parts omitted.

Referring now to FIG. 1, the sensor portion of my infrared constituent analyzer and control system, indicated generally by the reference numeral 10, includes an upper sensor head 12 and a lower sensor head 14 disposed respectively above and below a moving web 16 of material such as paper. The upper sensor head 12 includes a source 18 of continuous infrared radiation, which is collimated by an optical system including a mirror 20 and a lens 22 and directed onto a portion of the upper surface of the web 16.

Referring now also to FIG. 4, a continuous filter wheel or disk indicated generally by the reference numeral 24 is provided with a continuous filter portion 28, the passband of which varies continuously with angular displacement between a low center wavelength of 1.0 micron and a high center wavelength of 3.5 microns. Filter disk 24 is so positioned in the optical path between source 18 and web 16 that rotation of the disk 24 by a stepper motor 26 positions a desired angular segment of the filter portion 28 in the optical path so as to transmit a corresponding narrow band of infrared radiation. Preferably, the filter portion 28 occupies a semicircular portion of the filter disk 24, while the oher half of disk 24 contains an optically opaque portion or mask 30. Mask 30 interrupts the infrared beam from source 18 for 180° of each rotation of the filter disk 24 to chop the infrared beam and thereby provide a reference of zero incident radiation for the infrared detectors to be described. Stepper motor 26 preferably rotates filter 24 at a speed of about 600 rpm, or 10 rotations per second, in response to a signal provided on a line 152. Filter disk 24 is also formed with a peripheral lip 32 extending perpendicularly of the central portion of the disk. Lip 32 is formed with an aperture 34 at a point adjacent a suitable location, such as the 1.0 micron end of the continuous filter portion 28, so that an optical detector 36 responsive to the passage of aperture 34 can provide a signal on a line 150 to the signal processing circuit to be described indicating that the disk 24 has reached a predetermined angular position.

While the use of a continuous filter disk is especially desirable in the embodiment shown, it is also possible to use a wheel having a multiplicity of discrete monochromating interference filters, the exact number of filters depending on the number of wavelengths being sampled.

A cylindrical light pipe 38 directs radiation from the source 18 through a window 40, formed of sapphire or other material transparent to infrared radiation between 1.0 and 3.5 microns, onto the upper surface of the web 16. Reflected (or, more properly, backscattered) infrared radiation from the web portion irradiated by source 18 is collected by an integrating sphere 42, coaxial with light pipe 38, having a lower aperture 44 for collecting the reflected radiation and a diffusely reflective inner surface for spatially integrating the collected radiation without regard to its precise angle of reflection. A portion of the radiation collected by sphere 42 ultimately impinges upon an infrared detector 50 mounted in a housing 52 carried on the side of the sphere 42. Integrating sphere 42 is formed with a side aperture 46 for allowing the collected infrared radiation to impinge on the detector 50. A long-pass filter 48 positioned in front of the detector 50 filters out spurious radiation of shorter wavelengths, such as visible radiation, which may otherwise affect the measurement.

Referring now also to FIG. 3, a standard wheel 54 disposed between integrating-sphere aperture 44 and window 40 is selectively rotated by a stepper motor 56 controlled by a signal line 158 to position one of a plurality of standard samples 60, 62, 64, 66 and 68 in the optical path during a calibration sequence. Samples 60 to 68 contain stable components of the constituent or constituents to be measured in the web 16. For example, in the case of moisture measurements, the wheel 54 would contain five samples 60 to 68 of hydrated salts with specific moisture levels equivalent to those to be monitored in the moving web. Similarly, in the case of plastic coating measurement, there would be samples of plastic sealed in the standard wheel 54. Sample wheel 54 is also provided with an aperture 58 which is positioned in the optical path during normal operation, as shown in FIG. 1. A position encoder 57 provides a signal on a line 156 indicating the instantaneous position of the sample wheel 54.

In the lower sensor head 14, a second integrating sphere 72 is formed with an upper aperture 74 for collecting radiation transmitted through (or, more accurately, scattered forwardly from) the portion of web 16 irradiated by source 18. A window 70 of material similar to that of window 40 covers aperture 74 to protect the interior of sphere 72. Sphere 72 spatially integrates the transmitted radiation from the web 16 in manner similar to that of sphere 42. A second detector 80 disposed in a housing 82 mounted on the side of sphere 72 receives a portion of the collected transmitted radiation through a side aperture 76 formed in sphere 72 and a long-pass filter 78 similar to filter 48.

Referring also to FIG. 5, the integrating sphere 72 and detector housing 82 of lower head 14 are enclosed by a hermetically sealed, generally cylindrical housing 84, preferably formed of stainless steel or other corrosion-resistant material. Housing 84 is formed with an aperture at its upper end for receiving window 70. Housing 84 carries an upper air guide or shoe 86 disposed above window 70 at a slight spacing therefrom. Air guide 86 is formed with a semicircular indentation 87 of slightly smaller diameter than that of window 70 so as to overlie the peripheral portion of the left half of the window 70 as viewed in FIG. 5. Guide 86 directs air supplied to the interior of housing 84 by way of a connecting hose 88, and issuing from housing 84 through an upper aperture 89 (FIG. 1), across the upper face of the window 70 to clean the window 70 of any dirt or the like which may have settled upon its surface. A signal cable 90 leading from housing 84 contains the various signal lines conveying sensor information from, or control information to, the head 14. A similar housing (not shown) is provided for the upper head 12.

Figure 2:
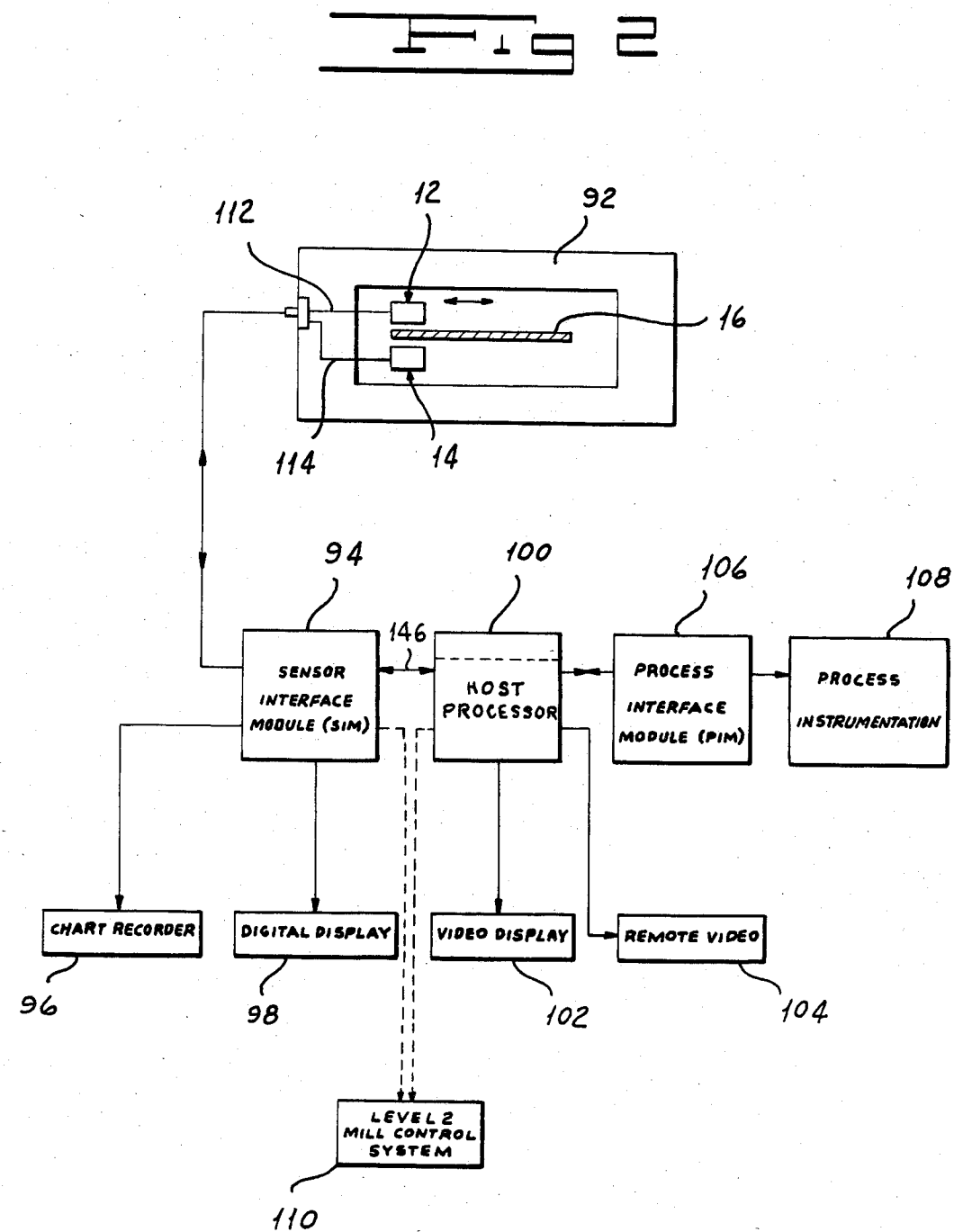
FIG. 2 is a schematic diagram of the infrared analyzer and control system incorporating the sensor heads shown in FIG. 1.

Referring now to FIG. 2, sensor heads 12 and 14 are preferably carried by a mechanical scanner 92 which is suitably actuated to move the heads transversely as a unit across the width of the web 16 to measure various portions thereof. Respective lines 112 and 114 from detectors 50 and 80 of upper and lower sensor heads 12 and 14 are coupled, along with the other electrical lines leading from heads 12 and 14, to a sensor interface module (SIM) 94, shown in more detail in FIG. 6. Sensor interface module 94 operates in a manner to be described to sample the outputs of detectors 50 and 80 at various positions of filter wheel 24 for ultimate conversion to indications of constituent content by a host processor 100 coupled to the module 94. In addition to receiving information from detectors 50 and 80, module 94 monitors and controls the positions of filter wheel 24 and sample wheel 54, and controls the temperatures of detectors 50 and 80. Sensor interface module 94 also provides outputs to suitable display devices such as a chart recorder 96 and a digital display 98, which may be used to display such information as detector temperatures or the like.

The host processor 100, which converts the detector outputs to constituent content measures, provides outputs indicating these quantities to suitable display devices such as a local video display 102 and a remote video display 104. Host processor 100 also communicates with the process instrumentation 108 by way of a process interface module (PIM) 106. Finally, both the host processor 100 and the sensor interface module 94 may communicate with a different-level mill-control system 110. Since the internal structures of the elements shown in FIG. 2 are generally conventional and do not, as such, form part of my invention, they have not been shown.

Referring now to FIG. 6, in the sensor interface module 94, I couple the outputs of detectors 50 and 80 via respective lines 112 and 114 to dc level restorers 120 and 122 through respective preamplifiers 116 and 118. A multiplexer 124 alternately gates signals from restorers 120 and 122 to a sample-and-hold circuit 126. Level restorers 120 and 122 supply multiplexer 124 with signals that are referenced to the outputs of detectors 50 and 80 with the opaque portion 30 of filter wheel 24 in the optical path, thereby compensating for spurious sources of infrared radiation. Circuit 126 provides an input to an analog-to-digital converter (ADC) 128. A microprocessor 130 controls the digitization of the incoming analog signals, and is provided with a local scratch-pad random-access memory (RAM) 132, a read-only memory (ROM) 134 for storage of the operating program, and an interrupt control 138 for handling asynchronous signals from sources such as position encoder 36. A local data bus 136 couples microprocessor 130 to the various devices of the module 94. The digitized values from ADC 128 are stored on alternate data-gathering cycles in buffer memory banks 140 and 142 controlled by a bus switch control 144. A host bus 146 couples bus switch control 144 to host processor 100. Host processor 100 processes the data stored in one of the memories 140 and 142 while microprocessor 130 is filling the other with digitized values from ADC 128.

The sensor interface module 94 monitors and controls the temperature of detectors 50 and 80 through suitable temperature control units 160 and 162. In a manner shown in my prior U.S. Pat. No. 4,171,918, control units 160 and 162 provide temperature control signals on respective lines 168 and 170 to heating and cooling units (not shown) of housings 52 and 82 to vary the dc resistance of respective detectors 50 and 80, thereby to provide accurate temperature control. Error signals supplied to units 160 and 162 on respective lines 164 and 166 may be derived from any suitable source, such as the detector outputs themselves on lines 112 and 114. The position of the sample wheel 54 is also controlled by the microprocessor 130 through a suitable control unit 154, responsive to encoder 57 via line 156, which actuates stepper motor 56 via line 158 to position each sample in its turn below the light pipe 38 during the calibration sequence. The filter wheel 24 is rotated and synchronized by the microprocessor 130 through a filter position control 148 providing an output to stepper motor 26 on line 152 and receiving an input from encoder 36 via line 150. Filter wheel 24, as mentioned above, may make 600 revolutions per minute, with the position encoder 36 providing a positional indication once per revolution.

In the absence of scattering, the relationship between the intensity $I_0$ of radiation incident upon a material and the transmitted radiation intensity $I_T$ is given by the expression $$I_T = I_0 \exp(-Kx) \tag{1}$$

where x is the thickness of the material and K is the absorption coefficient per unit thickness (1/m) of the material at the wavelength in question. The absorption coefficient K is in turn determined by the relation $$K = \Sigma k_j d_j \tag{2}$$

where $k_j$ is the mass absorption coefficient (m²/g) of the jth constituent and $d_j$ is its density (g/m³) in the material. Since the mass per unit area $m_j$ of the jth constituent is determined by the relation $$m_j = d_j x \tag{3}$$

we can rewrite equation (1) as $$I_T = I_0 \exp(-\Sigma k_j m_j) \tag{4}$$

This relationship is sometimes referred to as Beer's law.

In practice, one also has to take into account the effects of scattering, leading to a more complicated series of relationships generally referred to as the Kubelka-Munk equations. Thus, in a material where scattering is also present, the reflected and transmitted radiation intensities $I_R$ and $I_T$ are respectively given by the equations $$I_R/I_0 = R = 1/(a + b \coth bSx) \tag{5}$$

$$I_T/I_0 = T = (a-R)^2 - b^2 \tag{6}$$

where $$a = 1 + K/S = 1 + Kx/Sx \tag{7}$$

$$b = (a^2 - 1)^{\frac{1}{2}} \tag{8}$$

$$S = \Sigma s_j d_j \tag{9}$$

with $s_j$ being the mass scattering coefficient (m²/g) of the jth constituent and $I_0$, x, K and $d_j$ being defined as before.

Equations (2) and (9) can be rewritten as $$Sx = \Sigma s_j m_j \tag{10}$$

$$Kx = \Sigma k_j m_j \tag{11}$$

Equations (5) and (7) can accordingly be rewritten as $$I_R/I_0 = R = 1/(a + b \coth b \Sigma s_j m_j) \tag{12}$$

$$a = 1 + \Sigma k_j m_j / \Sigma s_j m_j \tag{13}$$

With this background, the following procedure is preferably used to determine the mass per unit area $m_j$ of the various web constituents from the measurements $I_R$ and $I_T$ of reflected and transmitted radiation at various wavelengths between 1.0 and 3.5 microns. First, the reflectance $R_i$ and transmittance $T_i$ of the web 16 are measured at each wavelength i of a multiplicity of substantially equally spaced wavelengths, preferably about 64 in number, between 1.0 and 3.5 microns to provide infrared reflectance and transmittance spectra. For each measured pair of $R_i$ and $T_i$, the web absorption $K_i x$ for that wavelength is calculated by solving equations (5) to (8) for Kx to provide a measured absorption spectrum insensitive to elastic scattering. Finally, the individual constituent contents $m_j$ are calculated from equation (11) using the method of least squares—that is, by least-square fitting the predicted absorption spectrum, with the estimated contents $m_j$ of the assumed constituents, to the measured absorption spectrum $K_i x$.

As an alternative to this preferred method, only the reflectances $R_i$ or transmittances $T_i$ may be measured, and the individual constituent contents $m_j$ calculated from equations (5) to (13) above by least-square fitting the predicted reflectance or transmittance spectrum to the corresponding measured spectrum. All of the assumed web constituents may be measured simultaneously using one of these methods, or only some or even one of the constituents, such as water, with the contents of the remaining constituents being assumed or measured using other sensors.

Figure 7:
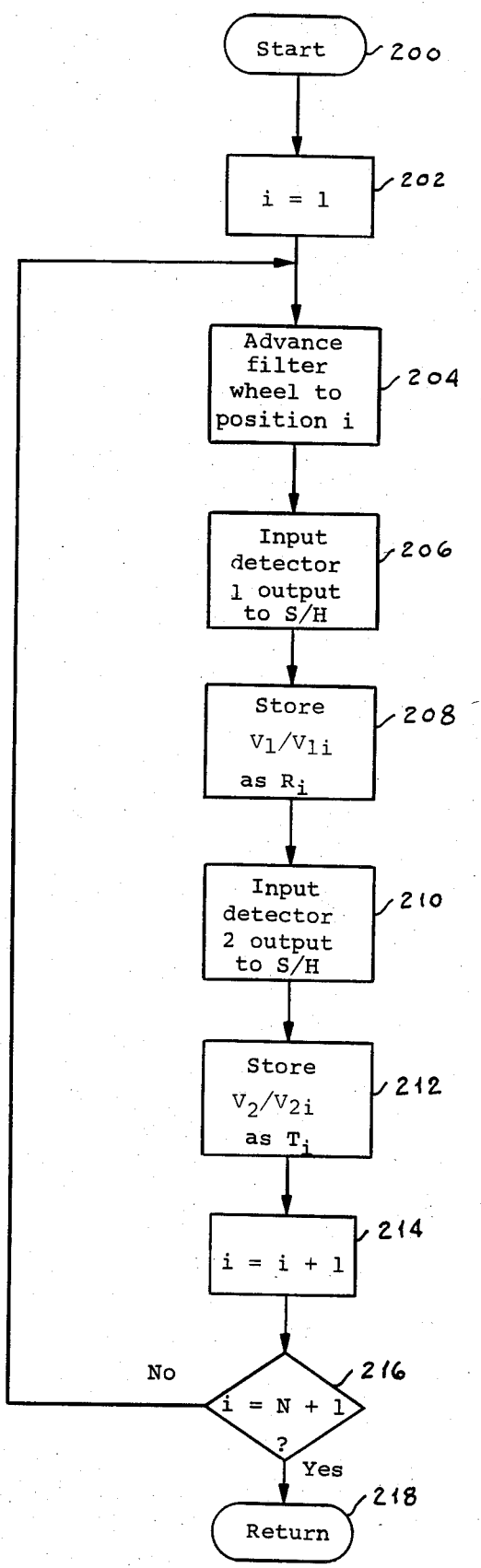
FIG. 7 is a flowchart illustrating the data-collecting routine of the circuit shown in FIG. 6.

Referring now to FIG. 7, I show the routine followed by microprocessor 130 for collecting the outputs from detectors 50 and 80 at various positions of the filter wheel 24 in preparation for conversion of these outputs to constituent contents by host processor 100. Upon entering the routine (step 200), microprocessor 130 initializes an index i indicating the position of the filter wheel 24 (step 202). Preferably, each of the detector outputs is sampled at 64 different positions of filter wheel 24 to provide a desirable number of measurements for further processing. These positions of filter wheel 24 are correlated with wavelength by means of a calibration table (not shown) stored in memory. The routine then enters a loop i which it advances the filter wheel 24 to the position indicated by the index i by actuating filter position control 148 to energize the stepper motor 26 a suitable number of times (step 204). In the course of advancing wheel 24 to the first position, at 1.0 micron, stepper motor 26 will have also rotated the opaque portion 30 through the optical pulse to provide the necessary reference for level restorers 120 and 122. After the filter wheel 24 has been advanced to position i, microprocessor 130 actuates multiplexer 124 to apply the output $V_1$ of level restorer 120, corresponding to the output of detector 50, to the input of sample-and-hold circuit 126 (step 206). The routine then divides the output of ADC 128 by a previously stored quantity $V_{1i}$ corresponding to the output of level restorer 120 at the ith position of filter wheel 24 for a perfectly reflective web 16; the quotient, representing the measured reflectance $R_i$ at that wavelength, is stored in whichever of buffer memories 140 and 142 is currently being filled (step 208).

Next, the routine applies the output $V_2$ of level restorer 122, corresponding to the output of detector 80, to the input of sample-and-hold circuit 126 (step 210). The routine then divides the output of ADC 128 by a previously stored quantity $V_{2i}$ representing the output of detector 80 with the web 16 removed from the space between sensor heads 12 and 14. The routine stores the quotient thus obtained, representing the measured transmittance $T_i$ at that wavelength, at a suitable location in buffer memory 140 or 142 (step 212). The quantity $V_{2i}$, like $V_{1i}$, may be obtained by any suitable means during a calibration sequence of sensor 10. The routine then increments the index i (step 214), and tests to determine whether the filter wheel 24 has been advanced through all of the positions of filter portion 28 in the optical path (step 216). If not, the routine advances the filter wheel 24 to the next position (step 204), and proceeds in the manner described above. When the filter wheel has been advanced through all its positions, the microprocessor 130 exits from the loop and returns (step 218) to the calling program (not shown), eventually for another pass through the same routine.

Figure 8:
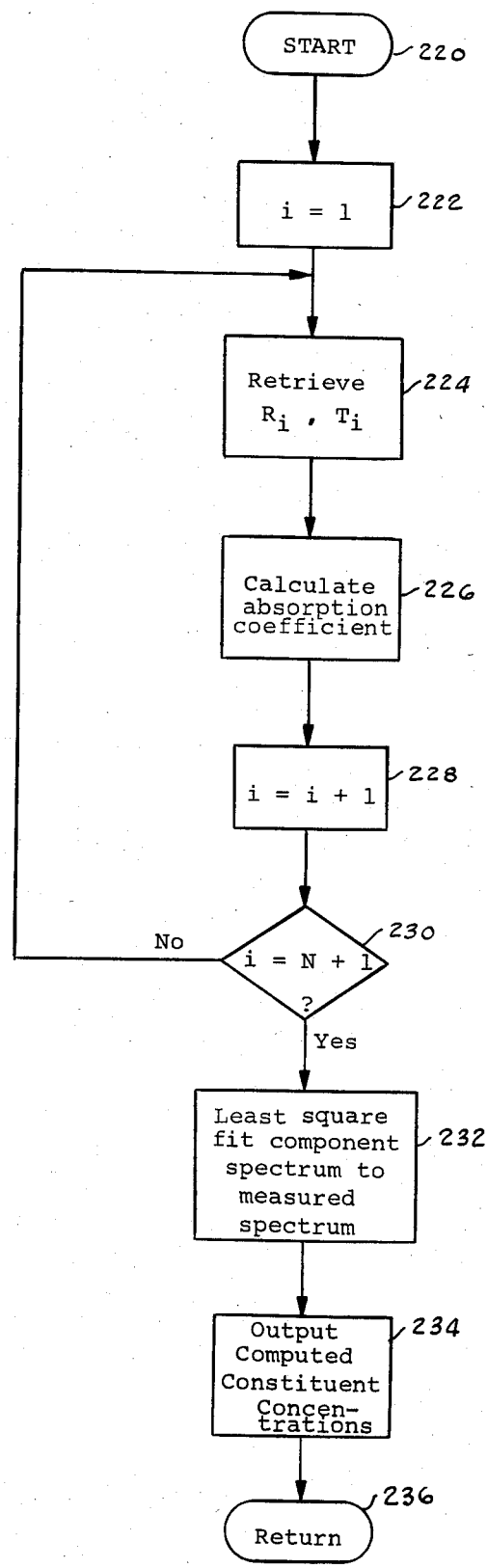
FIG. 8 is a flowchart illustrating the data-analyzing routine of the system shown in FIG. 2.

Referring now to FIG. 8, I show the routine simultaneously executed by the host processor 100 to convert previously obtained reflectance and transmittance measurements to indications of the concentrations of the constituents of web 16. Upon entering the routine (step 220), host processor 100 initializes an index i representing the particular wavelength at which the reflectance and transmittance measurements $R_i$ and $T_i$ were made. After retrieving the stored reflectance $R_i$ and transmittance $T_i$ from the buffer memory 140 or 142 not currently being filled by microprocessor 130 (step 224), the routine calculates the total absorption $K_i x$ of the web 16 at that wavelength, using equations (5) to (8) above (step 226). The routine then increments the index i (step 228), and tests to establish whether all of the wavelengths have been serviced (step 230). If other wavelengths remain to be serviced, the routine retrieves the stored reflectance $R_i$ and transmittance $T_i$ for the next wavelength (step 224) and proceeds in the manner described above.

When all the wavelengths have been serviced in this manner, the routine will have calculated a measured spectrum of absorption $K_i x$ of the web 16 for wavelengths between 1.0 and 3.5 microns. The routine then calculates the contents $m_j$ of the various constituents of the web 16 by least-square fitting the absorption spectra of the individual components, composed of the individual absorption coefficients $k_j$, to the total measured absorption spectrum $K_i x$ of the web 16 (step 232). Stated somewhat differently, the routine determines those estimated constituent contents $m_j$ which minimize the total square error between the predicted absorption spectrum $K_i x$ of the web 16, calculated on the basis of equation (11) above, and the measured absorption spectrum of the web 16 determined during steps 224 to 230. After the routine has determined estimated constituent contents or concentrations $m_j$ in this manner, the routine outputs these quantities to display devices 102 and 104, as well as to the process instrumentation 108 by way of process interface module 106 (step 234). Thereafter, the host processor 100 returns to the calling program (step 236), eventually for another pass through the same routine.

The procedure for least-square fitting is well known in the art, being disclosed, for example, in McCarty et al U.S. Pat. No. 3,601,589, as well as in my copending application Ser. No. 240,171, filed Mar. 3, 1981, now U.S. Pat. No. 4,439,038 entitled "Method and Apparatus for Measuring and Controlling the Color of a Moving Web." Accordingly, this least-square procedure has not been set forth in detail in FIG. 8.

As noted above, rather than determining the constituent concentrations from the absorption spectrum derived from the reflectance and transmittance spectra, one may also determine the concentrations by least-square fitting the appropriate constituent spectra to the reflectance or transmitted spectrum above. Since the relation between constituent concentration and reflectance or transmittance is, as shown above, highly nonlinear, an iterative method of least-square fitting is preferably employed. Such an iterative method is disclosed in the McCarty patent identified above.

It will be seen that I have accomplished the objects of my invention. I have provided a constituent analyzer which produces a direct measurement of the constituents of a moving web by measuring the concentrations of additives exhibiting either resonant absorption or preferential scattering over a range of infrared frequencies. My constituent analyzer has both backscatter and forward scatter measurement capability, and thus permits compensation for the effects of scattering. My analyzer permits regular automatic calibration for the various additives being measured. In addition, my system prevents dirt and dust from interfering with the measurement operation.

It will be understood that certain features and subcombinations are of utility and may be employed without reference to other features and subcombinations. This is contemplated by and is within the scope of my claims. It is further obvious that various changes may be made in details within the scope of my claims without departing from the spirit of my invention. It is, therefore, to be understood that my invention is not to be limitd to the specific details shown and described.

Having thus described my invention, what I claim is:

1. Apparatus for measuring a constituent of a material including in combination means for directing infrared radiation upon a portion of said material, means for measuring infrared radiation reflected from said portion to produce a reflection signal, means for measuring infrared radiation transmitted through said portion to produce a transmission signal, said transmission signal having a dependence on elastic scattering of said radiation by said material, means responsive to said transmission signal for generating an indication of the content of said constituent, and means responsive to said reflection signal for correcting said content indication for the dependence of said transmission signal on elastic scattering.

2. Apparatus as in claim 1 in which said constituent has predetermined absorption and scattering coefficients, said generating means comprising means responsive to said measuring means for deriving a quantity dependent only on said absorption coefficient and means for generating said indication as a function of said quantity.

3. Apparatus as in claim 1 in which said measuring means respectively comprise means for measuring the spectrum of infrared radiation reflected from said portion and means for measuring the spectrum of infrared radiation transmitted through said portion.

4. Apparatus as in claim 1 in which said measuring means respectively comprise means for measuring the spectrum of infrared radiation reflected from said portion and means for measuring the spectrum of infrared radiation transmitted through said portion, said generating means comprising means responsive to said measuring means for determining the absorption spectrum of said portion of said material and means for generating said indication as a function of said absorption spectrum.

5. Apparatus as in claim 1 in which said measuring means respectively comprise means for measuring the spectrum of infrared radiation reflected from said portion and means for measuring the spectrum of infrared radiation transmitted through said portion, said generating means comprising means responsive to said measuring means for determining the measured absorption spectrum of said material and means for determining from said measured absorption spectrum that estimated constituent content producing a minimum deviation between the predicted absorption spectrum of said material with said content of said constituent and said measured absorption spectrum.

6. A method of measuring a constituent of a material including the steps of directing infrared radiation upon a portion of said material, obtaining a measurement of infrared radiation reflected from said portion, obtaining a measurement of infrared radiation transmitted through said portion, said transmitted radiation measurement having a dependence on elastic scattering of said radiation by said material, generating an indication of the content of said constituent of said material in accordance with said transmitted radiation measurement, and correcting said content indication for the dependence of said transmitted radiation measurement on elastic scattering in accordance with said reflected radiation measurement.

7. A method as in claim 6 in which said constituent has predetermined absorption and scattering coefficients, said generating step including the steps of deriving from said measurements a quantity dependent only on said absorption coefficient and generating said indication as a function of said quantity.

8. A method as in claim 6 in which said measurements are spectrum measurements.

9. A method as in claim 6 in which said measurements are spectrum measurements, said generating step including the steps of determining the absorption spectrum of said portion of said material as a function of said spectrum measurements and generating said indication as a function of said absorption spectrum.

10. A method as in claim 6 in which said measurements are spectrum measurements, said generating step including the steps of determining the measured absorption spectrum of said material as a function of said spectrum measurements and determining from said measured absorption spectrum that estimated constituent content producing a minimum deviation between the predicted absorption spectrum of said material with said content of said constituent and said measured absorption spectrum.

11. Apparatus for measuring the content of a constituent of a web of material including in combination means for irradiating said web with infrared radiation, means for measuring the intensity of infrared radiation transmitted through said web to produce a transmission signal, said transmission signal having a dependence on elastic scattering of said radiation by material in said web, means for measuring the intensity of infrared radiation reflected from said web to produce a reflection signal, means responsive to said transmission signal for generating an indication of the content of said constituent, and means responsive to said reflection signal for correcting said content indication for the dependence of said transmission signal on elastic scattering.

12. Apparatus as in claim 11 in which each of said measuring means measures the intensity of a narrow band of radiation emanating from said web.

13. Apparatus as in claim 11 in which each of said measuring means measures the intensity of an essentially monochromatic band of radiation emanating from said web.

14. Apparatus as in claim 11 in which each of said measuring means measures the intensities of a plurality of narrow bands of radiation emanating from said web.

15. Apparatus as in claim 11 in which each of said measuring means measures the spectrum of infrared radiation emanating from said web.

* * * * *